United States Patent [19]
Kawai

[11] Patent Number: 5,594,771
[45] Date of Patent: Jan. 14, 1997

[54] DIGITAL ANGIOGRAPHIC APPARATUS

[75] Inventor: Masumi Kawai, Kusatsu, Japan

[73] Assignee: Shimadzu Corporation, Kyoto, Japan

[21] Appl. No.: 449,955

[22] Filed: May 25, 1995

[51] Int. Cl.$^6$ ............................................. H05G 1/64
[52] U.S. Cl. ................................ 378/98.2; 378/98.12
[58] Field of Search ............................ 378/98.12, 98.2, 378/98.11, 62, 9

[56] References Cited

U.S. PATENT DOCUMENTS

| | | | |
|---|---|---|---|
| 4,432,370 | 2/1984 | Hughes. | |
| 4,672,651 | 6/1987 | Horiba et al. | 378/9 X |
| 4,675,731 | 6/1987 | Takasu et al. | 378/98.12 X |
| 5,125,018 | 6/1992 | Asahina | 378/98.12 |
| 5,161,178 | 11/1992 | Honda et al. | 378/98.12 |

FOREIGN PATENT DOCUMENTS

| | | | |
|---|---|---|---|
| 0041752 | 12/1981 | European Pat. Off. . | |
| 0374328 | 6/1990 | European Pat. Off. . | |
| 06205296 | 7/1994 | Japan | 378/98.12 |
| WO93/15658 | 8/1993 | WIPO . | |

OTHER PUBLICATIONS

Medical Physics, vol. 18, No. 5, Sep. 1991 New York, pp. 972–977, S. Rudin et al "Improving Fluoroscopic Image Quality With Continuously Variable Zoom Magnification".

*Primary Examiner*—David P. Porta
*Attorney, Agent, or Firm*—Nikaido, Marmelstein, Murray & Oram LLP

[57] ABSTRACT

A focusing voltage and a defocusing voltage are selectively applied to a focus adjusting electrode of an image intensifier included in a fluoroscopic device. An image in focus is picked up when the focusing voltage is applied to the focus adjusting electrode, and this image is used as a live image. On the other hand, an image out of focus is picked up when the defocusing voltage is applied to the focus adjusting electrode. With a degree of being out of focus set appropriately, the image obtained may be an image of a site, e.g. a blood vessel, from which high frequency components are removed. This image is used as a mask image. After the patient is injected with contrast material, the voltages are switched for application to the focus adjusting electrode to pick up successively the mask image with application of the defocusing voltage, and the live image with application of the focusing voltage. Consequently, the interval of time between the two image pickup steps is shortened, and contrast material is not injected during the interval, to reduce the possibility of movement of the patient during the interval. A slip or deviation between the mask image and live image is diminished to suppress artifacts appearing in a subtraction image thereby acquired.

20 Claims, 9 Drawing Sheets

FIG.3A HAND SWITCH 60

FIG.3B VOLTAGE SWITCHER 40

FIG.3C HIGH VOLTAGE APPLICATION (PULSED X-RAY IRRADIATION)

FIG.5A HAND SWITCH 60

FIG.5B VOLTAGE SWITCHER 40

FIG.5C HIGH VOLTAGE APPLICATION (PULSED X-RAY IRRADIATION)

DIGITAL ANGIOGRAPHIC APPARATUS

BACKGROUND OF THE INVENTION (1) Field of the Invention

This invention relates to digital angiographic apparatus for picking up mask images and live images, and acquiring subtraction images through a subtraction between these mask images and live images.

(2) Description of the Related Art

Conventionally, angiography with a digital angiographic apparatus of this type is performed in the following sequence. First, a mask image is picked up without injecting the patient with contrast material, and this mask image is stored in memory. Then, after injecting contrast material, a live image is picked up and stored in memory. In a subsequent process, the mask image and live image stored in memory are subjected to a subtraction to acquire a subtraction image (blood vessel image).

Mask images and live images may be picked up of a plurality of sites by shifting a positional relationship between an X-ray tube/image intensifier and the patient along or around the body axis of the patient. Then, a plurality of subtraction images of these sites are acquired by subjecting the mask images and live images to subtractions. These mask images and live images are picked up in two separate steps, and the subtraction images are acquired therefrom in a subsequent process.

Specifically, mask images are first picked up of a plurality of predetermined sites while varying a positional relationship between the patient without contrast material injected and the X-ray tube and the like. These mask images are stored in memory. Then, after injecting the patient with contrast material, live images of the same sites are picked up while shifting the positions relationship between the patient and the X-ray tube and the like along the same locus as for picking up the mask images. The live images are also stored in memory. Subsequently, the mask images and live images stored are subjected to a subtraction for each site to acquire a subtraction image of each site.

The conventional apparatus with the above construction has the following drawbacks.

According to the conventional apparatus, mask images are picked up and stored in advance and, after the injecting the patient with contrast material, live images are picked up and stored. Subtraction images are acquired in a subsequent process. Such a procedure provides a low throughput.

It is necessary to inject the patient with contrast material between mask image pickup and live image pickup. The patient could easily move during the intervening period. A movement of the patient brings about a deviation of the positional relationship between the patient and the X-ray tube and the like. This results in a slip between mask image and live image. Consequently, artifacts could appear in the subtraction images thereby produced.

In particular, where angiography is performed for a plurality of sites while varying the positional relationship between the patient and the X-ray tube and the like, mask images and live images are picked up of the respective sites in two separate steps. After picking up a mask image of one site and before picking up a live image of the same site, there occurs at least an interval of time which is a sum of time required for varying the positional relationship between the patient and the X-ray tube and the like and time required for injecting the patient with contrast material. The patient is likely to move during this extended time from mask image pickup to the live image pickup for the same site.

In addition, each live image must be picked up by shifting the positional relationship between the patient and the X-ray tube and the like along the same locus as for the mask image pickup, and must be picked up of the same site as the mask image was picked up. A disagreement tends to occur between two image pickup sites from the question of mechanical precision of a mechanism for shifting the positional relationship. The resulting subtraction image is vulnerable to artifacts.

With the conventional apparatus, therefore, a plurality of imaging sites are determined at fine intervals in performing angiography for these sites while shifting the positional relationship between the patient and the X-ray tube and the like. A plurality of mask images and live images are picked up of each of the sites determined at fine intervals. In a subsequent process, a mask image and a live image matching or close to each other are searched and retrieved. This pair of images are subjected to a subtraction to acquire a subtraction image with reduced artifacts.

However, numerous images unnecessary for medical examination are picked up when a plurality of mask images and live images are picked up of each of the sites determined at fine intervals. To pick up such unnecessary images, X rays irradiate the patient wastefully, and the patient unduly suffers increased exposure to X rays.

SUMMARY OF THE INVENTION

This invention has been made having regard to the state of the art noted above, and its object is to provide a digital angiographic apparatus which assures an excellent processing throughput, suppresses artifacts appearing in subtraction images as a result of a slip between mask image and live image, and involves no image pickup unnecessary for medical examination to relieve patients from excessive exposure to X rays.

The above object is fulfilled, according to a first aspect of this invention, by a digital angiographic apparatus for picking up a mask image and a live image of a predetermined site, and deriving a subtraction image from a subtraction between the mask image and the live image, the apparatus comprising:

(a) a fluoroscopic device including an X-ray tube and an image intensifier for irradiating a patient with X rays, and picking up fluoroscopic images of the patient;

(b) a signal converting device for converting the fluoroscopic images into digital data;

(c) an image storage device for storing the fluoroscopic images (images picked up) converted into digital data;

(d) a voltage switching device switchable between a position for applying a focusing voltage to a focus adjusting electrode of the image intensifier, and a position for applying a defocusing voltage to the focus adjusting electrode;

(e) a computing device for deriving a subtraction image from a subtraction between a mask image picked up when the defocusing voltage is applied to the focus adjusting electrode, and a live image picked up when the focusing voltage is applied to the focus adjusting electrode; and (f) a control device for controlling the fluoroscopic device and other devices to apply the defocusing voltage (or the focusing voltage) to the focus adjusting electrode, to pick up the mask image (or the live image) of the predetermined site of the patient with contrast material injected, to store at least the mask image (or the live image) in the image storage device, thereafter to switch the voltage switching device to the position for applying the focusing voltage (or the defocusing voltage) to the focus adjusting electrode, to pick up the live image (or the mask image) of the predetermined site, and to apply the mask image and the live image to the computing device to acquire the subtraction image for the predetermined site.

With this apparatus, the control device controls the voltage switching device to switch in a predetermined order between the position for applying the defocusing voltage to the focus adjusting electrode, and the position for applying the focusing voltage thereto. In the respective positions, the control device controls the fluoroscopic device and signal converting device to pick up a mask image, with application of the defocusing voltage, and a live image, with application of the focusing voltage, of a predetermined site of a patient having contrast material injected. Whichever of the mask image and live image may be picked up first. That is, whichever of the defocusing voltage and focusing voltage may be applied to the focus adjusting electrode first. At least the image picked up first is stored in the image storage device. The image picked up later may also be stored in the image storage device. The control device applies to the computing device the image (mask image or live image) picked up first and stored in the image storage device, and the image (live image or mask image) picked up later (or the live or mask image picked up later and stored in the image storage device). The pair of mask image and live image are subjected to a subtraction to acquire a subtraction image for the site.

An image out of focus is picked up when the defocusing voltage is applied to the focus adjusting electrode of the image intensifier. By appropriately setting a degree of being out of focus according to the site, high frequency components may be removed from the image of the site, e.g. a blood vessel. Thus, with an appropriate degree of being out of focus, an image of a blood vessel or the like free from high free frequency components is obtained by picking up the image of the patient having contrast material injected. On the other hand, high frequency components remain an in-focus image picked up, with application of the focusing voltage to the focus adjusting electrode, of the patient having contrast material injected. The image out of focus, and the image in focus, picked up of the patient having contrast material injected, are used as the mask image and the live image, respectively. These images are subjected to a subtraction to acquire a subtraction image (of the blood vessel).

This invention acquires the subtraction image on the above principle, from the mask image and live image picked up of the patient with contrast material injected, by switching the voltages applied to the focus adjusting electrode. It is unnecessary to secure time for injecting the patient with contrast material between mask image pickup and live image pickup. The mask image and live image are picked up simply by switching the voltages applied to the focus adjusting electrode. Consequently, the interval of time between the two image pickup steps is shortened. This reduces the possibility of movement of the patient during the interval. A slip or deviation between the mask image and live image is diminished to suppress artifacts appearing in the subtraction image thereby acquired.

The mask image and live image are picked up within a short time, and immediately thereafter the two images are subjected to a subtraction to acquire a subtraction image. Thus, the subtraction image is acquired in real time, and the process has an excellent throughput.

The degree of being out of focus varies with sites of the patient to be imaged. For example, the head has relatively thin blood vessels. The degree of being out of focus is set low to remove blood vessel images of this region. The chest, the abdomen and the like have relatively thick blood vessels such as arteries. Images of such blood vessels cannot be removed without setting a certain high degree of being out of focus. The thickness of blood vessels differs also between child and adult. The degree of being out of focus should preferably be higher when images are picked up of an adult than when images are picked up of a child.

It is, therefore, preferable that the voltage switching device is switchable between a position for applying the focusing voltage to the focus adjusting electrode, and a position for applying plural types of defocusing voltages thereto, the control device being operable, when picking up the mask image, to select one of the defocusing voltages for application to the focus adjusting electrode according to imaging conditions such as the predetermined site and the patient to be imaged. Then, an excellent mask image may be acquired from different patients (adult and child) by suitably selecting the defocusing voltages through the voltage switching device.

In a second aspect of the invention, there is provided a digital angiographic apparatus for picking up mask images and live images of a plurality of predetermined sites of a patient by shifting a positional relationship between an X-ray tube/image intensifier and the patient, and deriving a subtraction image for each of the sites from a subtraction between the mask image and the live image of each site, the apparatus comprising:

(a) a fluoroscopic device including the X-ray tube and the image intensifier for irradiating the patient with X rays, and picking up fluoroscopic images of the patient;

(b) a signal converting device for converting the fluoroscopic images into digital data;

(c) an image storage device for storing the fluoroscopic images (images picked up) converted into digital data;

(d) a voltage switching device switchable between a position for applying a focusing voltage to a focus adjusting electrode of the image intensifier, and a position for applying a defocusing voltage to the focus adjusting electrode;

(e) a computing device for deriving a subtraction image from a subtraction between each mask image picked up when the defocusing voltage is applied to the focus adjusting electrode, and each live image picked up when the focusing voltage is applied to the focus adjusting electrode;

(f) a position shifting device for shifting the positional relationship between the patient and the X-ray tube/image intensifier; and (g) a control device for controlling the fluoroscopic device and other devices to shift the positional relationship between the patient with contrast material injected and the X-ray tube/image intensifier, and each time the positional relationship reaches one of the predetermined sites of the patient, to apply the defocusing voltage (or the focusing voltage) to the focus adjusting electrode, to pick up the mask image (or the live image), to store at least the mask image (or the live image) in the image storage device, thereafter to switch the voltage switching device to the position for applying the focusing voltage (or the defocusing voltage) to the focus adjusting electrode, to pick up the live image (or the mask image) of the predetermined site, and to apply the mask image and the live image to the computing device to acquire the subtraction image for each of the predetermined sites.

This apparatus is based on the same principle as the apparatus in the first aspect of the invention described above.

The positional relationship between the patient with contrast material injected and the X-ray tube/image intensifier of the fluoroscopic device is shifted. Each time the positional relationship reaches one of predetermined sites of the patient, a pair of images (a mask image and a live image) are picked up in a predetermined order. The pair of images are subjected to a subtraction to acquire a subtraction image of the site. That is, the positional relationship between the patient with contrast material injected and the X-ray tube and the like is shifted once, and a mask image and a live image are picked up of each site. These mask image and live image are subjected to a subtraction to acquire a subtraction image of the site. The number of shifts made in the positional relationship between the patient and the X-ray tube and the like is lessened to a half of the number of shifts required of the conventional apparatus. There is no need for injecting the patient with contrast material during the process. This suppresses artifacts appearing in each subtraction image, and provides an excellent throughput of the process.

Where the positional relationship between the patient and the X-ray tube and the like is continuously shifted during the mask image pickup and live image pickup for each site, the pair of images are picked up in slightly displaced positions. However, the relative shift between the patient and the X-ray tube and the like is much slower than the speed of picking up each image. Thus, a displacement occurring when each image is picked up is slight. Besides, one of the images subjected to the subtraction is a blurred image. The slight slip of the images due to the displacement is absorbed by this blur. Consequently, the slight displacement occurring when the pair of images are picked up presents no problem for practical purposes.

It is preferred that the shift in the positional relationship between the patient and the X-ray tube and the like is temporarily stopped while the pair of images are picked up of each site. That is, the positional relationship between the patient and the X-ray tube and the like is shifted stepwise to eliminate the slip between the pair of images picked up of each site.

With this apparatus, only the sites necessary for diagnostic purposes may be selected for imaging, to acquire subtraction images of these sites, without picking up unnecessary images as in the conventional apparatus. In addition, the patient is protected from excessive exposure to X rays.

As noted hereinbefore, the degree of being out of focus varies with sites of the patient to be imaged. It is, therefore, preferable that, in the apparatus in the second aspect of the invention, the voltage switching device is switchable between a position for applying the focusing voltage to the focus adjusting electrode, and a position for applying plural types of defocusing voltages thereto, the control device being operable, when picking up the mask image of each site, to select one of the defocusing voltages for application to the focus adjusting electrode according to imaging conditions such as the site and the patient to be imaged. Then, for example, excellent mask images may be obtained for securing excellent subtraction images of a relatively wide range of sites including those sites requiring varied degrees of being out of focus.

BRIEF DESCRIPTION OF THE DRAWINGS

For the purpose of illustrating the invention, there are shown in the drawings several forms which are presently preferred, it being understood, however, that the invention is not limited to the precise arrangements and istrumentalities shown.

DETAILED DESCRIPTION OF THE PREFERRED EMBODIMENTS

Preferred embodiments of this invention will be described in detail hereinafter with reference to the drawings.

First Embodiment

An apparatus in a first embodiment will be described with reference to FIGS. 1, 2 and so on. The first embodiment corresponds to the invention defined in claim 1, which is constructed to acquire a subtraction image of a predetermined site.

Figure 1:
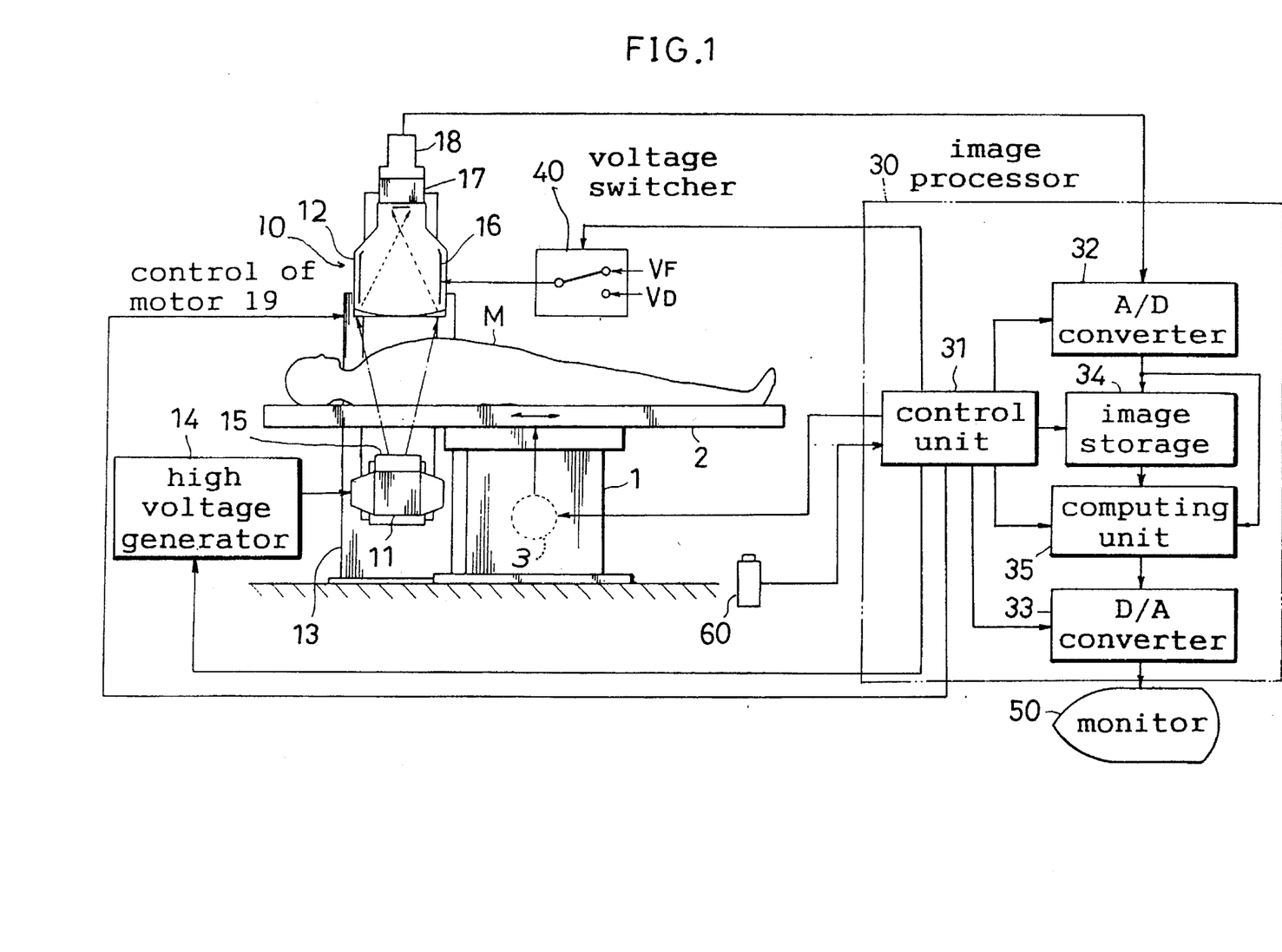
FIG. 1 is a front view of a digital angiographic apparatus in a first embodiment of this invention.
Figure 2:
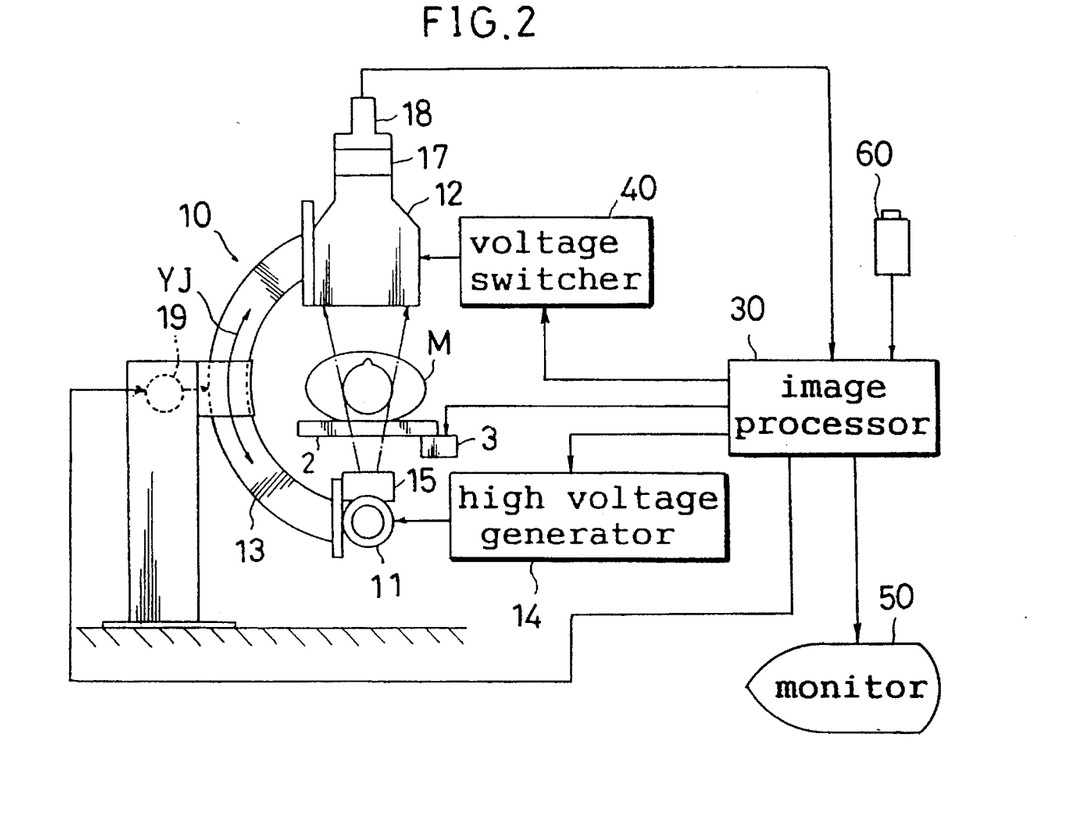
FIG. 2 is a side view showing a positional relationship between a fluoroscopic device in the first embodiment and a patient lying on a top board.

In FIG. 1, numeral 1 denotes a pedestal installed on a floor. The pedestal 1 has a top board 2 horizontally movably attached thereto for supporting a patient M lying thereon. The top board 2 is driven to move horizontally by a motor 3 mounted in the pedestal 1. The motor 3 is controlled by a control unit 31 included in an image processor 30 described later.

Numeral 10 denotes a fluoroscopic device disposed adjacent the pedestal 1. The fluoroscopic device 10 includes an X-ray tube 11 and an image intensifier 12. The X-ray tube 11 and image intensifier 12 are attached to opposite ends of C-shaped arm 13, and opposed to each other across the patient M lying on the top board 2. This C-shaped arm 13 is driven by a motor 19 to be movable about the body axis of patient M in directions of arrow YJ in FIG. 2. Thus, the patient M may be irradiated with pulsed X rays emitted from selected directions. This motor 19 is controllable by the control unit 31 described later.

A high voltage generator 14 is connected to the X-ray tube 11. The X-ray tube 11 generates pulsed X rays when power (X-ray tube voltage and X-ray tube current) is supplied to the X-ray tube 11 from the high voltage generator 14. Irradiation timing of pulsed X rays from the X-ray tube 11 is controlled by the control unit 31 described later, through the high voltage generator 14.

The pulsed X rays from the X-ray tube 11 are collimated by a collimator 15 to irradiate the patient M on the top board 2. X rays transmitted through the patient M enter the image intensifier 12. The X rays incident on the image intensifier 12 are reduced and amplified by an electron lens system including a focus adjusting electrode 16, and outputted as a visible light image. The outputted optical image is transmitted through an optical system 17 to a video camera 18. This video camera 18 converts the optical image into video signals of a fluoroscopic image for application to the image processor 30.

The focus adjusting electrode 16 of image intensifier 12 receives a focusing voltage VF or a defocusing voltage VD through a voltage switcher 40 acting as the voltage switch device. The switching operation of voltage switcher 40 is controlled by the control unit 31 described later.

The video signals (analog signals) of the fluoroscopic image applied to the image processor 30 are converted, under control of the control unit 31, into digital data by an A/D (analog-to-digital) converter 32 acting as the signal converting device. The image processor 30 includes an image memory 34 acting as the image storage device for storing images picked up, a computing unit 35 acting as the computing device for computing subtraction images, and the control unit 31 acting as the control device. The image processor 30, under control of the control unit 35, processes the fluoroscopic image (image picked up) in the digital data provided by the A/D converter 32 to compute a subtraction image. The subtraction image is converted into analog signals by a D/A (digital-to-analog) converter 33 for display on a monitor 50.

The control unit 31, on instructions from a control panel not shown, controls the motor 3 to move horizontally the patient M lying on the top board 2, to position a site to be imaged of patient M relative to the X-ray tube 11 and image intensifier 12 of fluoroscopic device 10. The control unit 31 controls also the motor 19 to adjust a direction of X rays for irradiating the patient M. After these adjustments, the control unit 31, upon receipt of a process starting instruction from a hand switch 60, controls the high voltage generator 14, voltage switcher 40, A/D converter 32, image memory 34, computing unit 35 and D/A converter 33 as follows, to compute a subtraction image of the imaged site positioned as above, with the irradiating direction of X rays adjusted, and to cause the subtraction image to be displayed on the monitor 50. It is to be noted that the patient M is injected with contrast material before the process starting instruction from the hand switch 60. Mask images and live images are picked up of the patent M injected with contrast material, as described later.

Figure 3A:
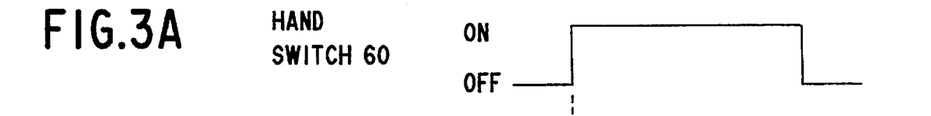
FIG. 3 is a time chart showing a control sequence of a control unit in the first embodiment.
Figure 3B:
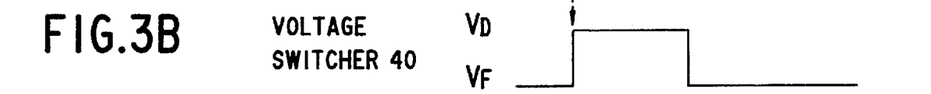
Figure 3C:
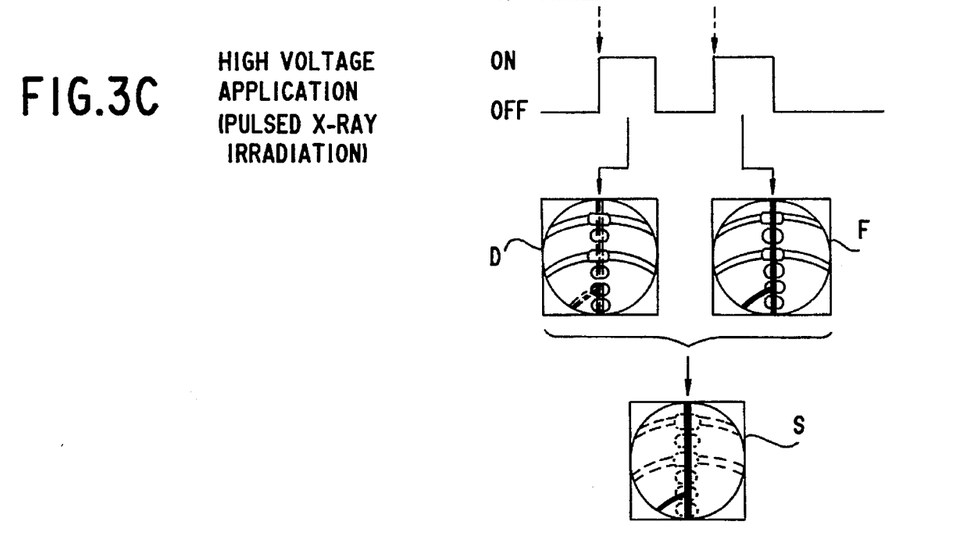

The controls by the control unit 31 will be described with reference to the time chart shown in FIG. 3.

When the hand switch 60 is pressed, "ON" signal is applied to the control unit 31 as a trigger. In response to the "ON" signal, the control unit 31 operates the voltage switcher 40 to apply defocusing voltage VD to the focus adjusting electrode 16. Upon completion of the operation of voltage switcher 40, the control unit 31 causes the high voltage generator 14 to supply power to the X-ray tube 11, whereby the X-ray tube 11 emits pulsed X rays.

The image D picked up by means of these pulsed X rays is a blurred image out of focus. With an appropriate degree of being out of focus, the image obtained may be an image of a site, e.g. a blood vessel, of patient M with contrast material injected, from which high frequency components are removed. The image picked up in this way, with high frequency components removed therefrom, may be used as mask image D. This mask image D is stored in the image memory 34. Once the mask image D is stored, the image memory 34 is placed in write-inhibited state.

Next, the voltage switcher 40 is operated to apply focusing voltage VF to the focus adjusting electrode 16. Upon completion of the operation of voltage switcher 40, the control unit 31 causes the high voltage generator 14 to supply power to the X-ray tube 11, whereby the X-ray tube 11 emits pulsed X rays.

The image F picked up by means of these pulsed X rays is in focus, which may be an image of the blood vessel of patient M with contrast material injected, which retains high frequency components. The image picked up in this way, with high frequency components retained therein, may be used as live image F. The control unit 31 applies this live image F to the computing unit 35. Synchronously therewith, the control unit 31 reads the mask image D from the image memory 34, and applies the mask image D to the computing unit 35. The computing unit 35 performs a subtraction between the mask image D and live image F. A resulting subtraction image S corresponds to the live image F from which only low frequency components are removed, and includes edges of bones or soft tissues and the blood vessel. The control unit 31 causes this subtraction image S to be displayed on the monitor 50, and finishes the imaging process.

As described above, the voltage switcher 40 is operated to switch voltages VD and VF for application to the focus adjusting electrode 16. In the respective states, images (mask image D and live image F) are picked up of the patient M with contrast material injected, to acquire subtraction image S. It is unnecessary to secure time for injecting the patient M with contrast material between mask image pickup and live image pickup as in the conventional apparatus. The mask image and live image may be picked up successively according to this invention. Consequently, the interval of time between the two image pickup steps is shortened to reduce the possibility of movement of the patient M during the interval. A slip or deviation between the mask image and live image is diminished to suppress artifacts appearing in subtraction image S thereby acquired. The mask image D and live image F are picked up successively. As soon as the live image F is picked up, subtraction image S is computed. Thus, subtraction image S is acquired in real time, and the process has an excellent throughput. Further, the subtraction image S acquired includes edges of bones or soft tissues as well as the blood vessel, and may be used advantageously as an orientation image for a surgical operation.

The degree of being out of focus in picking up the mask image D, i.e. a value of defocusing voltage VD applied to the focus adjusting electrode 16, needs to be a degree suited for removing an image of a blood vessel and the like. The degree of being out of focus varies with sites of patient M to be imaged. For example, the head has relatively thin blood vessels. The degree of being out of focus is set low to remove blood vessel images of this region. The chest, the abdomen and the like have relatively thick blood vessels such as arteries. Images of such blood vessels cannot be removed without setting a certain high degree of being out of focus. The thickness of blood vessels differs also between child and adult. The degree of being out of focus should preferably be higher when images are picked up of an adult than when images are picked up of a child.

Specifically, when 12-inch Image Intensifier, IA-12LM series (manufactured by Shimadz Corporation) was used as image intensifier 12, excellent mask images D, live images F and subtraction images S of varied sites were acquired by setting focusing voltage VF to AC 600 V for all the sites, and setting defocusing voltage VD to approximately AC 500 V for imaging the head, and to AC 350–400 V for imaging the chest and the abdomen. Where the patient M is a child, excellent mask images and the like are obtained by slightly increasing the above defocusing voltage VD to lower the degree of being out of focus slightly.

Figure 4:
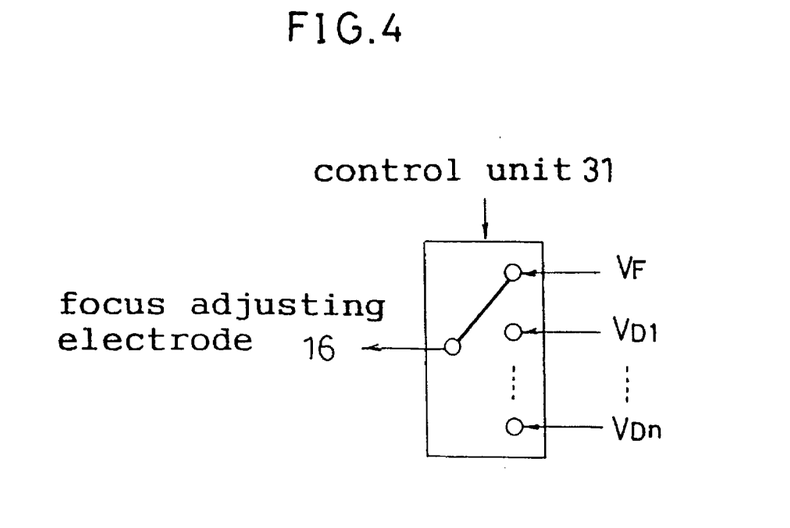
FIG. 4 is a view showing a modified voltage switcher.

The images of blood vessels remain in mask images when the defocusing voltage VD is set higher than optimal voltages for varied sites to be imaged. As a result, the images of blood vessels are removed from subtraction images S. It is therefore desirable for optimal defocusing voltage VD to be applied to the focus adjusting electrode 16 according to varied sites. In the construction shown in FIG. 1, one type of defocusing voltage VD is used so that the subtraction image S is acquired only for a particular site. Thus, the defocusing voltage VD applied through the voltage switcher 40 in FIG. 1 may be made variable. Or, as shown in FIG. 4, plural types of defocusing voltages VD1–VDn may be used selectively according to sites to be imaged and other imaging conditions. This produces a desirable effect of accommodating varied sites and imaging conditions simply by selecting an optimal defocusing voltage through the voltage switcher 40. The recitation in claim 4, "said voltage switching means is switchable between a position for applying said focusing voltage to said focus adjusting electrode, and a position for applying plural types of defocusing voltages thereto", refers to the variable feature of defocusing voltage VD through the voltage switcher 40 in FIG. 1, and the construction of voltage switch 40 as shown in FIG. 4.

Figure 5A:
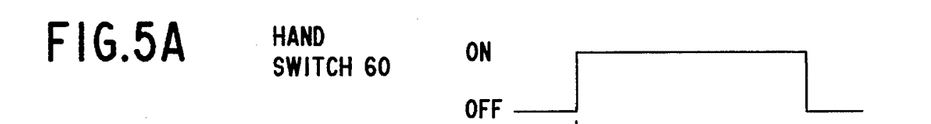
FIG. 5 is a time chart showing a different control sequence of the control unit in the first embodiment.
Figure 5B:
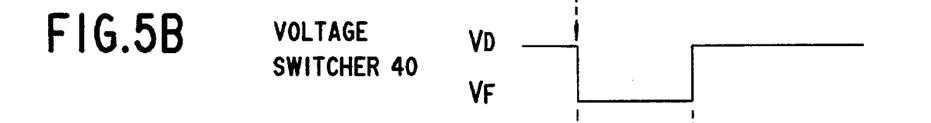
Figure 5C:
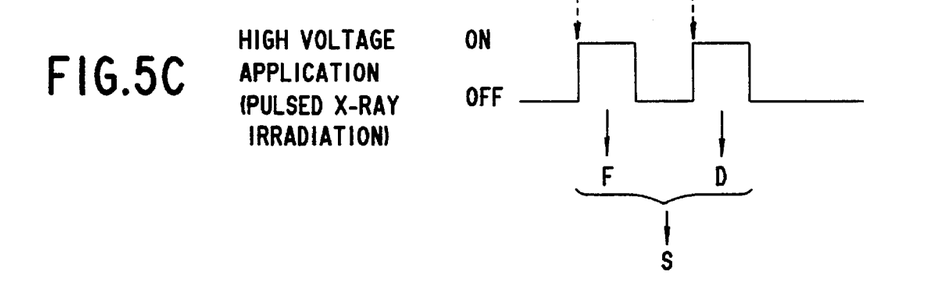

As described above, mask image D and live image F are both picked up after the patient M is injected with contrast material. Therefore, whichever image may be picked up first. Consequently, as shown in the time chart of FIG. 5, the voltage switcher 40 may be controlled to apply focusing voltage VF first to the focus adjusting electrode 16 to pick up live image F. The live image F is stored in the image memory 34. Subsequently, the voltage switcher 40 may be controlled to apply defocusing voltage VD to pick up mask image D. A subtraction is performed for the live image F (read from the image memory 34) and mask image D to acquire subtraction image S.

Figures 6A, 6B:
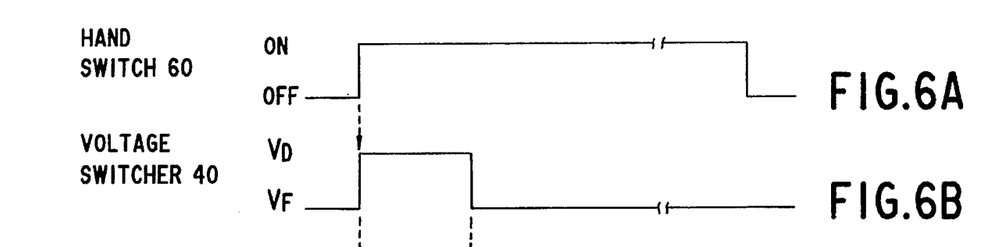
FIG. 6 is a time chart showing a further control sequence of the control unit in the first embodiment.

As shown in the time chart of FIG. 6, one mask image D may be picked up first, and stored in the image memory 34. Then, a plurality of live images of the same site may be picked up successively. Subtractions are performed for the mask image D and respective live images F1, F2, ... Fn ("n" being a natural number not less than 2), to acquire a plurality of subtraction images S1, S2, ... Sn of the same site. For example, mask image D is picked up immediately after injecting the patient M with contrast material, and live images F1, F2, ... Fn are picked up to show a manner in which the contrast material spreads in a blood vessel. Thus, the live images F1, F2, ... Fn enable an observation of variations occurring with time in which the contrast material spreads in the blood vessel.

When a subtraction is performed for mask image D and live image F to acquire subtraction image S, the mask image D may be multiplied by coefficient "k" as in $S=F-k \cdot D$ ($0 \leq k \leq 1$). As a result, edges of bones and soft tissues may be highlighted in the subtraction image S, to superpose, with emphasis, position information of a blood vessel image on the subtraction image S. Then, the subtraction image S will be more effective as an orientation image.

Figures 6C, 10:
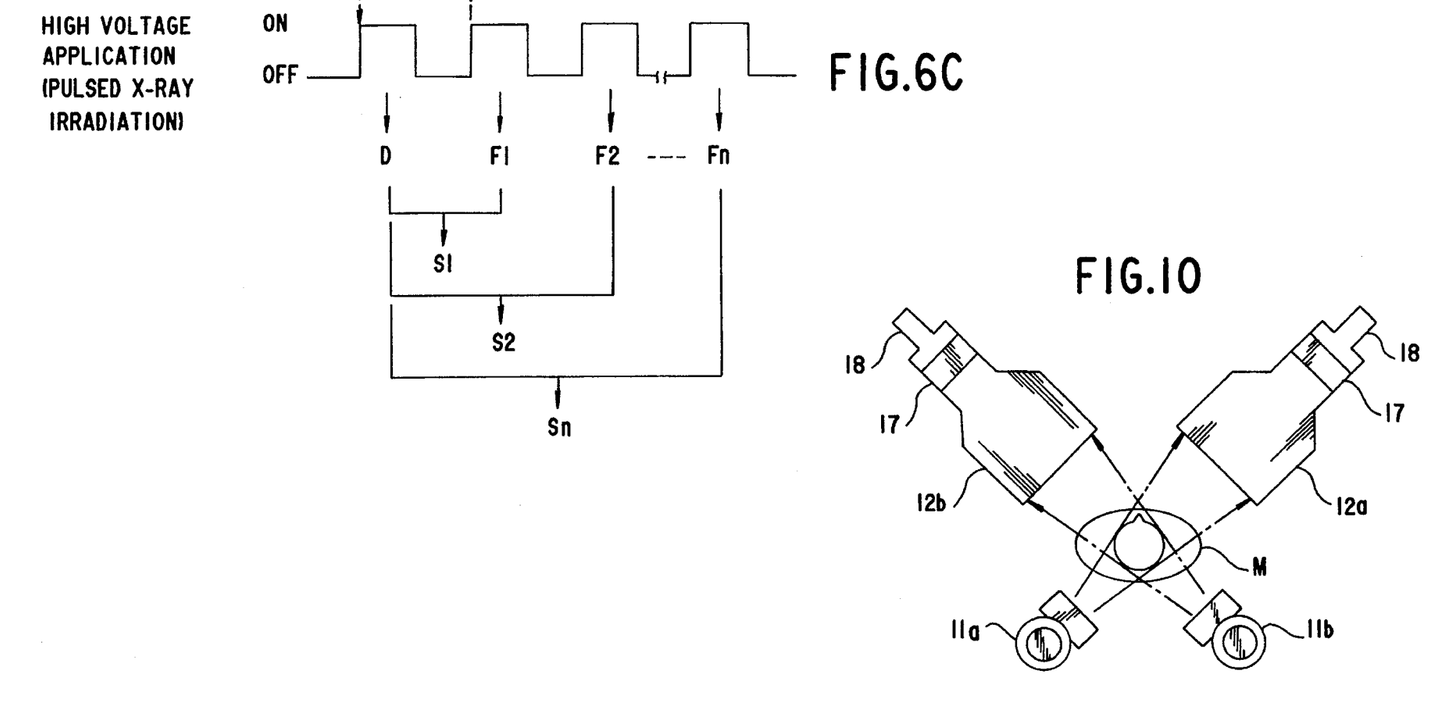
FIG. 10 is a side view schematically showing a construction for irradiating a patients site with X rays from two directions.
Figure 7:
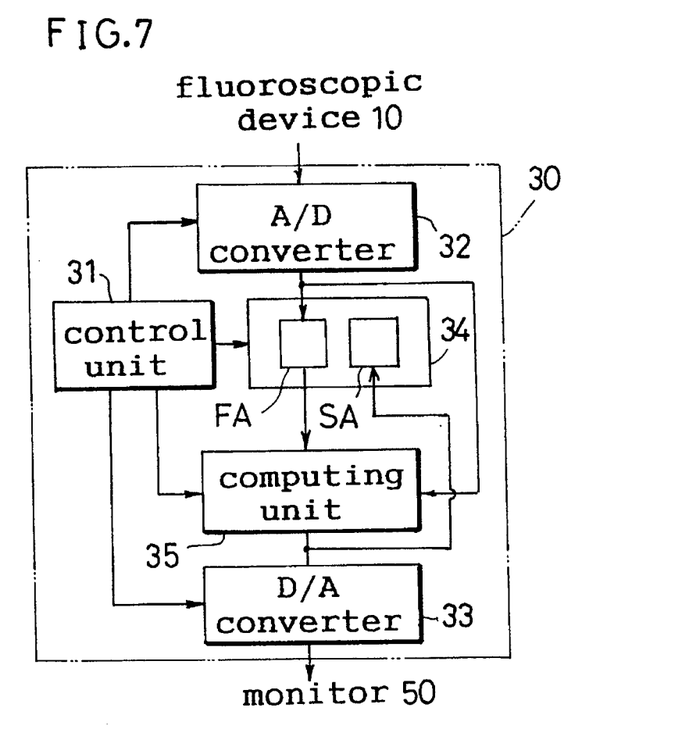
FIG. 7 is a block diagram of a modified image processor.

In the first embodiment described above, the subtraction image S acquired is displayed on the monitor 50. As shown in FIG. 7, the subtraction image S acquired, while being displayed on the monitor 50, may be stored in a storage location SA (different from a storage location FA for storing an image picked up first) in the image memory 34. This construction allows the subtraction image S to be subjected to subsequent data processing, or to be redisplayed on the monitor 50. Alternatively, the subtraction image S may be stored in an image processor or external storage separate from the image memory 34. The subtraction images S1, S2, ... Sn acquired as shown in FIG. 6 may also be stored in memory.

Figure 8:
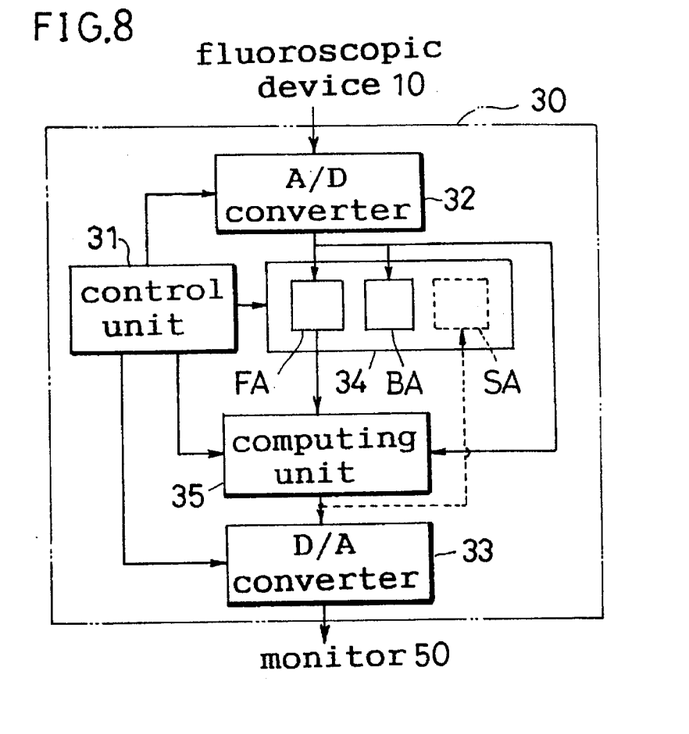
FIG. 8 is a block diagram of another modified image processor.

In the first embodiment and in the modification shown in FIG. 6, the image picked up later (live images F1–Fn in the case shown in FIG. 6) is applied to the computing unit 35 to compute subtraction image S. As shown in FIG. 8, the image picked up later, while being applied to the computing unit 35 to compute subtraction image S, may be stored in a storage location BA (different from storage location FA for storing the image picked up first) in the image memory 34 (or other storage). This construction allows the respective images stored in the image memory 34 to be subjected to subsequent data processing (e.g. to compute subtraction image S by subjecting mask image D to a filtering process to remove high frequency components, or to compute subtraction image S when desired). The respective images (mask image and live image) may be displayed on the monitor 50. As shown in a dotted line in FIG. 8, this construction may of course include the feature of the modification shown in FIG. 7, to store the subtraction image S determined by the computing unit 35, in a storage location SA (different from storage locations FA and FB) in the image memory 34.

Figure 9:
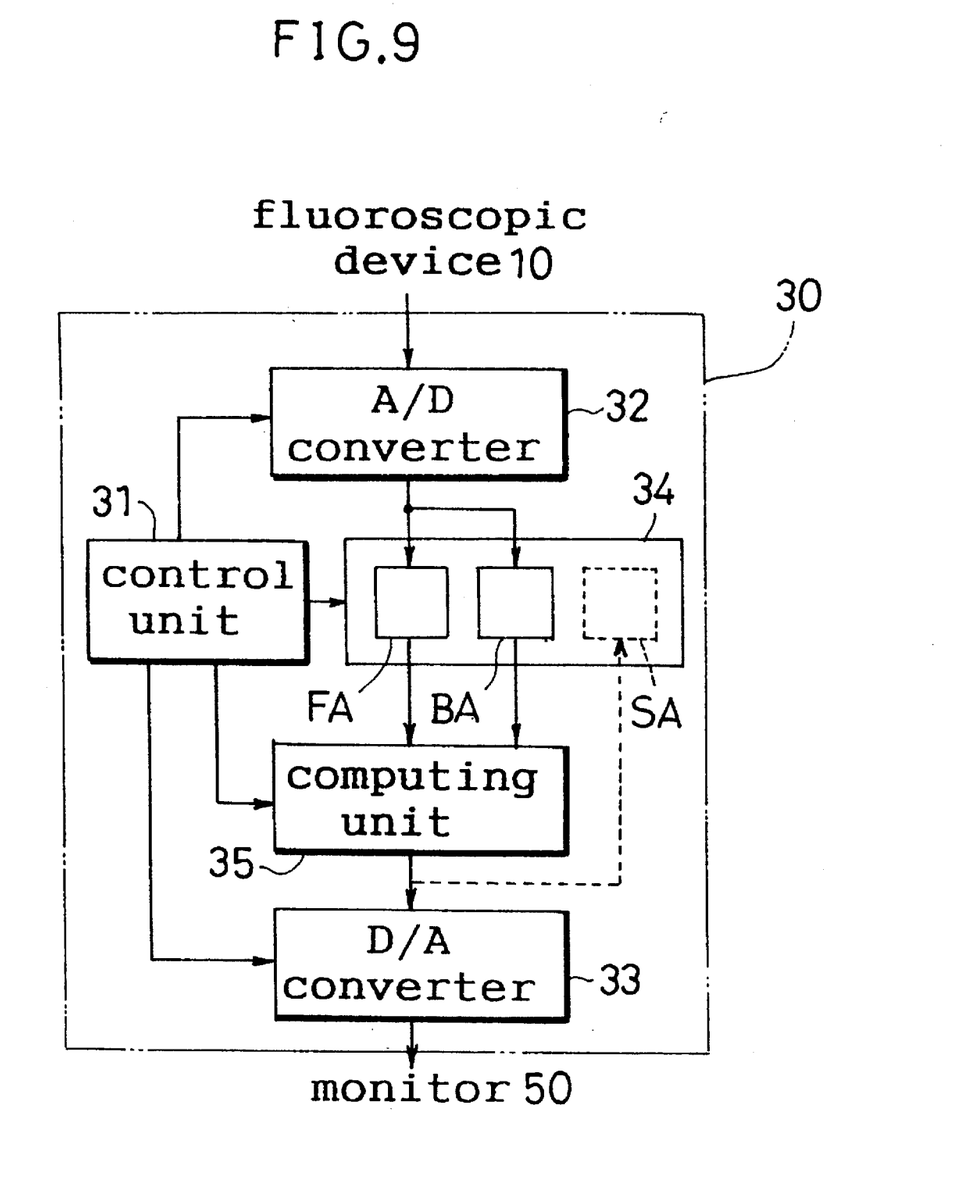
FIG. 9 is a block diagram of a further modified image processor.

As shown in FIG. 9, the image picked up later, instead of being applied to the computing unit 35, may be stored in a storage location BA (different from storage location FA for storing the image picked up first) in the image memory 34. In a subsequent process, the respective images (mask image D and live image F) may be applied to the computing unit 35 to compute a subtraction image S through a subtraction, and display the subtraction image S on the monitor 50. As noted hereinbefore the mask image D and live image F are picked up of patient M injected with contrast material. Thus, these images may be picked up successively. This construction provides a better throughput than the conventional apparatus even if subtraction image S is acquired in a subsequent process. In this modification also, the subtraction image S determined in a subsequent process may be stored in a storage location SA (different from storage locations FA and BA) in the image memory 34, to dispense with the trouble of computing subtraction image S all over again.

In the first embodiment and in the modifications thereof, images are picked up by irradiating a site with X rays emitted in one direction from the fluoroscopic device 10 having one set of X-ray tube 11 and image intensifier 12. As shown in FIG. 10, two sets of X-ray tube 11 and image intensifier 12 may be arranged around the patient M to irradiate a site with X rays emitted from two directions. Then, a subtraction image may be derived from a subtraction of images picked up in each direction. That is, X-ray tube 11a emits X rays, and image intensifier 12a picks up a mask image and a life image. A subtraction image in one direction is derived from a subtraction of these mask image and live image. X-ray tube 11b emits X rays, and image intensifier 12b picks up a mask image and a life image. A subtraction image in the other direction is derived from a subtraction of these mask image and live image. Thus, diagnostic information on a predetermined site may be acquired in a large amount. Needless to say, three or more sets of X-ray tube 11 and image intensifier 12 may be arranged around the patient M to acquire subtraction images in varied directions.

Second Embodiment

Figure 11:
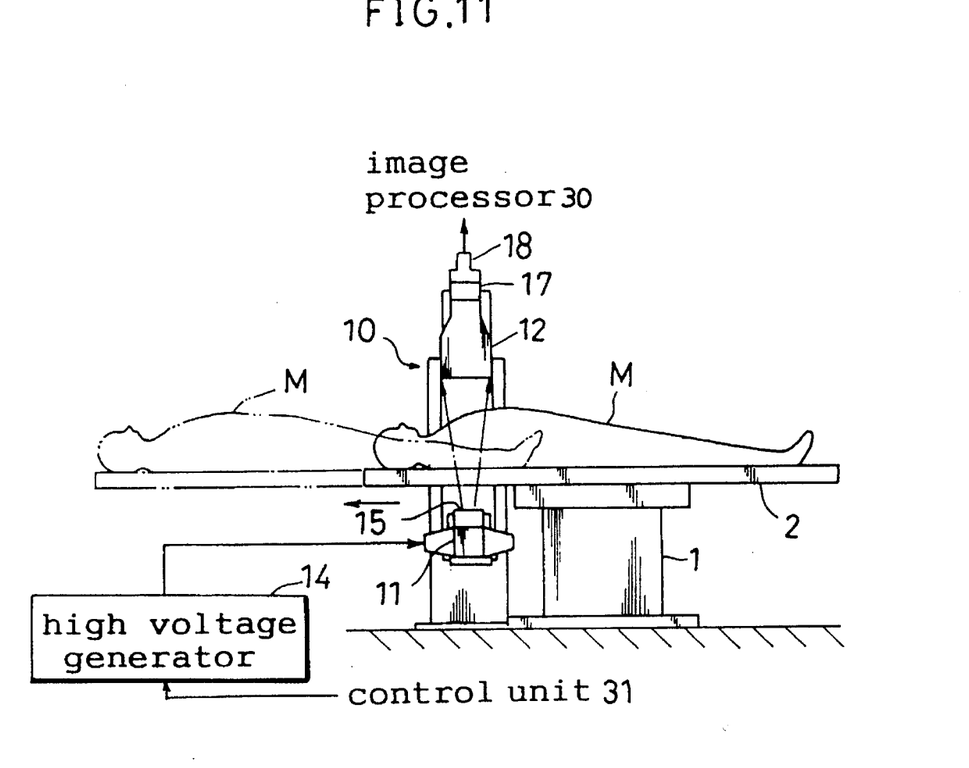
FIG. 11 is a front view showing an outline of an apparatus in the second embodiment of this invention.
Figure 12A:
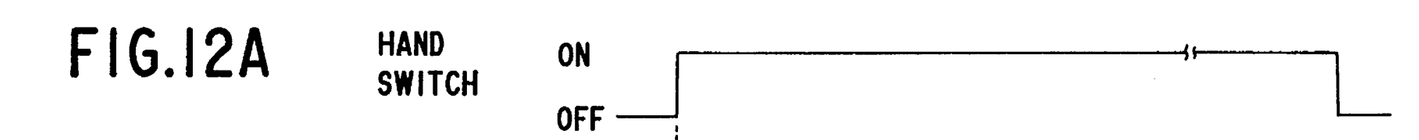
FIG. 12 is a time chart showing a control sequence of a control unit in the second embodiment.
Figure 12B:
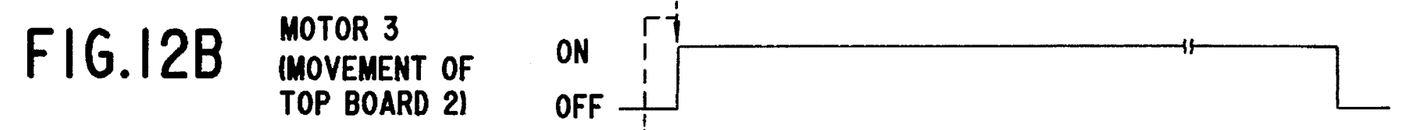
Figure 12C:
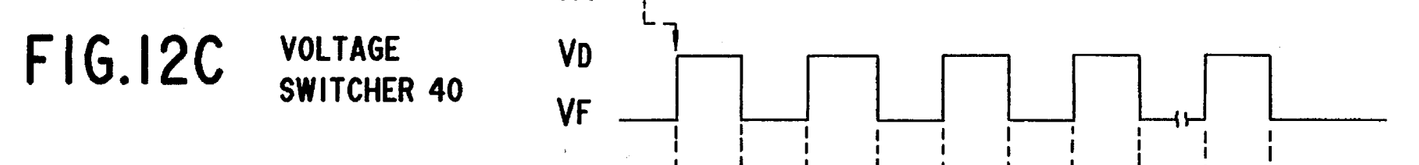
Figure 12D:
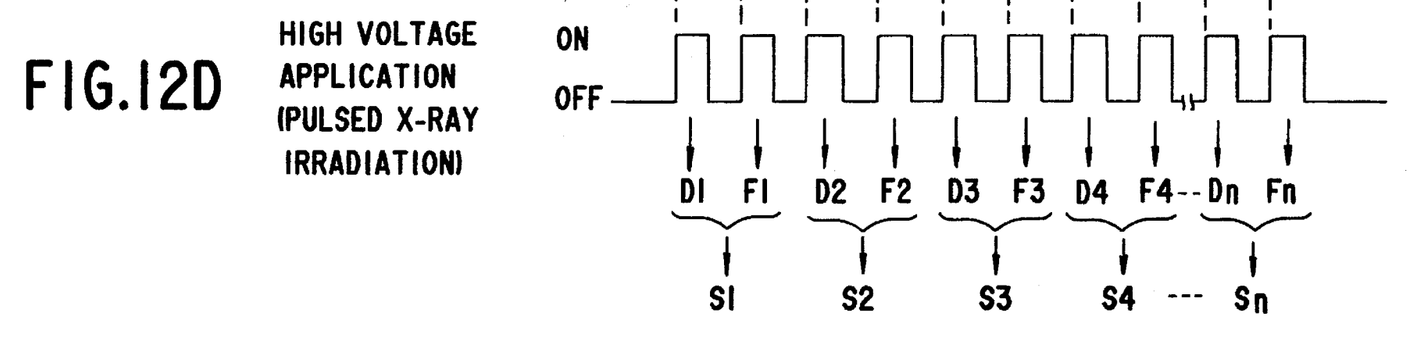

An apparatus in a second embodiment will be described with reference to FIGS. 11, 12 and so on. The second embodiment corresponds to the invention defined in claim 2, which is constructed to acquire subtraction images of a plurality of sites while varying a positional relationship between the patient and the X-ray tube/image intensifier of the fluoroscopic device.

The construction of the apparatus in the second embodiment is basically the same as in the first embodiment (see FIGS. 1 and 2), the difference being in the controls by the control unit 31. This aspect will be described, taking a construction as shown in FIG. 11, for example, where the positional relationship between the patient and the X-ray tube 11 and image intensifier 12 of fluoroscopic device 10 is shifted along the body axis of patient M. The motor 3 for horizontally moving the top board 2 in FIGS. 1 and 2 corresponds, in this case, to the position shifting means in claim 2.

The control unit 31, on instructions from the control panel not shown, controls the motor 3 to move horizontally the patient M lying on the top board 2 and having contrast material injected, to position a starting site to be imaged of patient M relative to the X-ray tube 11 and image intensifier 12 of fluoroscopic device 10. The control unit 31 controls also the motor 19 to adjust a direction of X rays for irradiating the patient M. In this state, the control unit 31, upon receipt of a process starting instruction from the hand switch 60, controls the high voltage generator 14, voltage switcher 40, A/D converter 32, image memory 34, computing unit 35, D/A converter 33 and motor 3 as follows, to compute subtraction images of a plurality of imaged sites predetermined, for example, through the control panel, while shifting the positional relationship between the patient M and the X-ray tube 11 and image intensifier 12 of fluoroscopic device 10 along the body axis of patient M, and to cause the subtraction images to be displayed on the monitor 50.

The controls by the control unit 31 will be described with reference to the time chart shown in FIG. 12.

When the hand switch 60 is pressed, "ON" signal is applied to the control unit 31 as a trigger. In response to the "ON" signal, the control unit 31 drives the motor 3 to move the top board 2 horizontally at a fixed rate (e.g. 200 mm/sec.), thereby to start shifting the positional relationship between the patient M with contrast material injected, and the X-ray tube 11 and image intensifier 12 of fluoroscopic device 10 along the body axis of patient M. When the positional relationship between the patient M and the X-ray tube 11 and image intensifier 12 of fluoroscopic device 10 reaches a first site to be imaged, the control unit 31 operates the voltage switcher 40 to apply defocusing voltage VD to the focus adjusting electrode 16. Upon completion of the operation of voltage switcher 40, the control unit 31 causes the high voltage generator 14 to supply power to the X-ray tube 11, whereby the X-ray tube 11 emits pulsed X rays. As a result, a blurred image out of focus is picked up and stored in the image memory 34. This image (out of focus) acts as a mask image D1 of the first site. Once the mask image D1 is stored, the image memory 34 is placed in write-inhibited state.

Next, the voltage switcher 40 is operated to apply focusing voltage VF to the focus adjusting electrode 16. Upon completion of this switching operation, the control unit 31 causes the high voltage generator 14 to supply power to the X-ray tube 11, whereby the X-ray tube 11 emits pulsed X rays to pick up an image in focus. This image (in focus) acts as a live image F1 of the first site. The control unit 31 applies this live image F1 to the computing unit 35. Synchronously therewith, the control unit 31 reads the mask image D1 from the image memory 34, and applies the mask image D1 to the computing unit 35. The computing unit 35 performs a subtraction between the mask image D1 and live image F1. This subtraction provides a subtraction image S1 of the first site. The subtraction image S1 acquired is displayed on the monitor 50. After the mask image D1 is read, the image memory 34 is reinstated in write-permitted state.

When a second site to be imaged of patient M reaches a position opposed to the X-ray tube 11 and image intensifier 12 of fluoroscopic device 10, the control unit 31 operates the voltage switcher 40 to apply defocusing voltage VD to the focus adjusting electrode 16 as above. As a result, a mask image D2 of the second site is picked up and stored in the image memory 34 (in write-permitted state at this time). Next, the voltage switcher 40 is operated to apply focusing voltage VF to the focus adjusting electrode 16, thereby to pick up live image F2 of the second site. The control unit 31 causes the computing unit 35 to perform a subtraction between this live image F2 and the mask image D2 of the second site read from the image memory 34. This subtraction provides a subtraction image S2 of the second site. The subtraction image S1 acquired is displayed on the monitor 50. After the mask image D2 is stored, the image memory 34 is placed in write-inhibited state. After the mask image D2 is read, the image memory 34 is reinstated in write-permitted state. Thus, only the mask image first picked up of each site is stored in the image memory 34. The different sites are set at intervals of several 10 to several 100 millimeters. The top board 2 is moved horizontally at the fixed rate. It is therefore possible to determine the time taken from an (i)th site ("i" being a natural number) to an (i+1)th site.

Thereafter, in sequences similar to the above, a subtraction image S3 is acquired for a third site, a subtraction image S4 for a fourth site, and a subtraction image Sn ("n" being a natural number not less than 2) for an "n"th site. These subtraction images are successively displayed on the monitor 50. When the depression of hand switch 60 is stopped (to apply "OFF" signal to the control unit 31), the process is terminated.

In the above control sequence, mask images Di is first picked up for each site. However, live image Fi may be picked up first.

Subtraction image Si may be computed based on $Si=Fi-k \cdot Di$ ($0 \leq k \leq 1$) for each site. Then, edges of bones and soft tissues may be highlighted in the subtraction images S1–Sn of the respective sites, to superpose, with emphasis, position information of a blood vessel image on the subtraction images S1–Sn.

As described above, the positional relationship between the patient M with contrast material injected, and the X-ray tube 11 and image intensifier 12 of fluoroscopic device 10 is shifted. Each time the positional relationship reaches one of the predetermined sites to be imaged, a pair of images (mask image Di and live image Fi) are picked up in a predetermined order. Subtraction image Si of each site is acquired from a subtraction between the pair of images. Thus, the positional relationship between the patient M with contrast material injected, and the X-ray tube 11 and the like, is shifted only once. The number of shifts made in the positional relationship between the patient M and the X-ray tube 11 and the like is lessened to a half of the number of shifts required of the conventional apparatus. There is no need for injecting the patient M with contrast material during the process. Consequently, a shortened time is interposed between the steps of picking up mask image Di and live image Fi for obtaining subtraction image Si for each site. This reduces the possibility of movement of the patient M during the interval. Artifacts hardly appear in subtraction image Si thereby obtained for each site. The process has an excellent throughput also.

As seen from the time chart in FIG. 12, the top board 2 is moved horizontally even during an image pickup (irradiation of pulsed X rays) for each site. A pulse width of X rays is small in the order of milliseconds, while the horizontal movement of top board 2 is slow at 200 mm/sec. Thus, blurring of each image due to the horizontal movement of top board 2 is negligible for practical purposes.

The top board 2 is moved horizontally between the steps of picking up mask image Di and live image Fi of each site. Thus, the two images are picked up in slightly displaced positions. Consequently, artifacts could appear in subtraction image Si derived from these images Di and Fi. However, the horizontal movement of top board 2 is effected at low speed as described above, whereas each image is picked up at high speed. Thus, a displacement occurring when each image is picked up is slight. Where, for example, the video camera 18 picks up images at the rate of 30 frames per second, one image is picked up in 1/30 second. On the other hand, where the speed of horizontal movement of top board 2 is 200 mm/sec., the shift between pickup positions of images Di and Fi is approximately 7 mm. Besides, one of the images subjected to a subtraction is a blurred image (Di). The slight slip of the images due to the displacement is absorbed by this blur. Consequently, the slight displacement occurring when images Di and Fi are picked up presents no problem for practical purposes. The sites need not be determined at fine intervals to secure the respective sites in register as in the conventional apparatus. Only the sites necessary for diagnostic purposes may be selected for imaging, without picking up unnecessary images. The patient M is thus protected from excessive exposure to X rays.

Figure 13A:
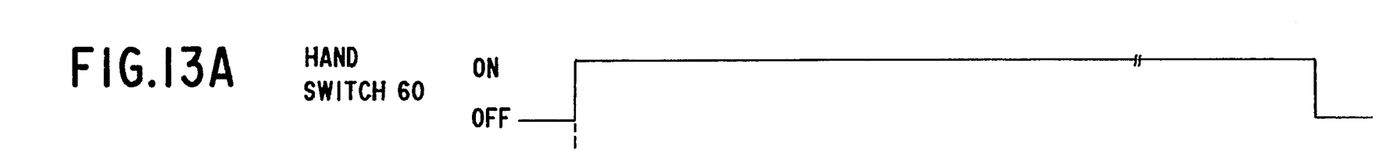
FIG. 13 is a time chart showing a different control sequence of the control unit in the second embodiment.
Figure 13B:
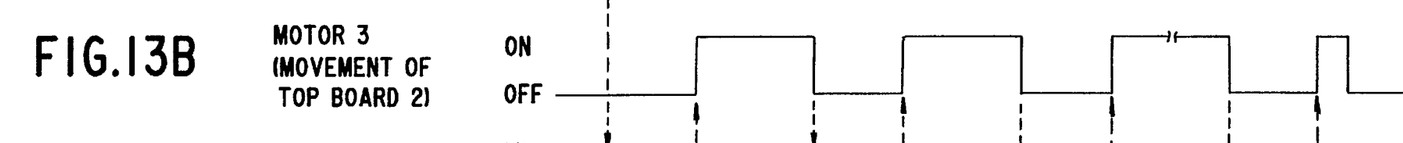
Figures 13C, 13D:
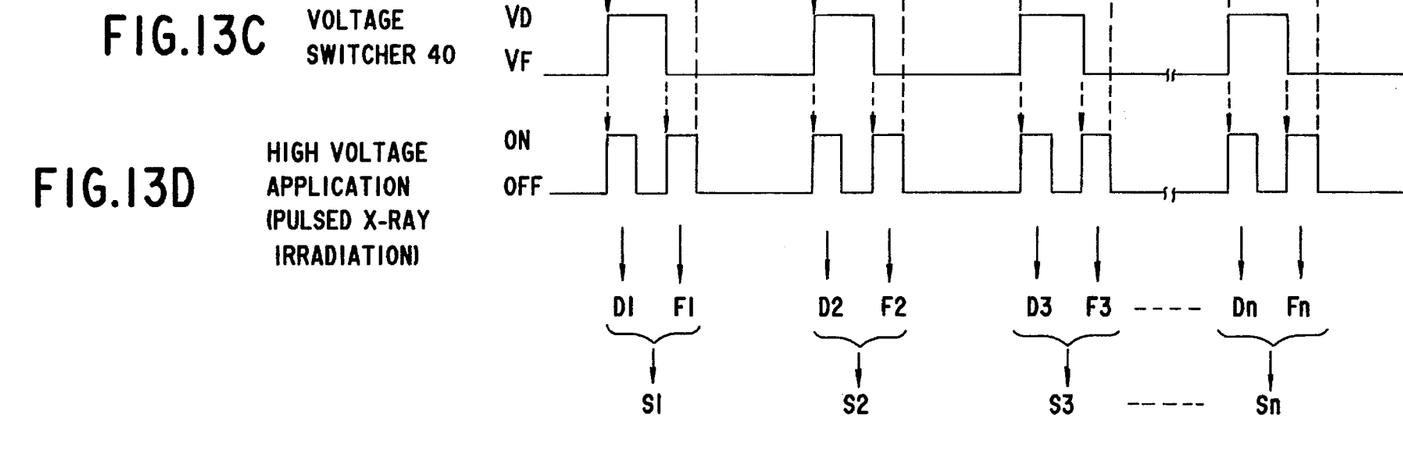

As shown in the time chart of FIG. 13, the control unit 31 may temporarily stop the horizontal movement of top board 2 while the pair of images Di and Fi are picked up of each site. This will completely eliminate inconveniences such as image blurring due to the horizontal movement of board 2 taking place during an image pickup (irradiation of pulsed X rays) for each site, and a displacement occurring when mask image Di and live image Fi are picked up of each site. This assures an improved image quality of subtraction image Si acquired for each site.

In the time chart shown in FIG. 13, when the hand switch 60 is pressed and the positional relationship between the patient and the X-ray tube 11 and the like reaches a first site, the control unit 31 stops the horizontal movement of top board 2 and, in this state, operates the voltage switcher 40 to switch the voltages applied. Pulsed X rays are emitted to pick up mask image D1 of the first site. This mask image D1 is stored in the image memory 34. Next, live image F1 of the same site is picked up to acquire subtraction image S1. When the emission of pulsed X rays to pick up the live image is completed, the control unit 31 resumes the horizontal movement of top board 2. When a second site is reached, the control unit 31 stops the top board 2. When the horizontal movement of top board 2 is stopped, mask image D2 of the second site is picked up by operating the voltage switcher 40, and stored in the image memory 34. Next, live image F2 of the second site is picked up to acquire subtraction image S2. Subsequently, the top board 2 is moved to image one site after another until the depression of hand switch 60 is terminated, to acquire subtraction images S1–Sn for a plurality of sites. In the control sequence of FIG. 13 also, live image Fi of each site may be picked up first.

In the control sequences of FIGS. 12 and 13, the process is finished when the depression of hand switch 60 is terminated. However, the process may be finished automatically when subtraction images have been obtained for all of the predetermined sites. Assume, for example, that sites are determined with intervals of 100 mm from the chest to the abdomen. The pressing of hand switch 60 is used merely as a trigger for starting the process. When the hand switch 60 is pressed, the top board 2 is moved horizontally to place the first site in the position opposed to the X-ray tube 11 and the like. When the first site reaches the position opposed to the X-ray tube 11 and the like, the first mask image D1 and live image F1 are picked up to acquire the first subtraction image S1. Then, as shown in FIG. 11, the top board 2 is moved horizontally leftward from the first site at the fixed rate (200 mm/sec.). Each time a subsequent site reaches the position opposed to the X-ray tube 11 and the like (every 0.5 second), mask image Di and live image Fi of that site are picked up to acquire subtraction image Si. Subtraction image Sm of the last site ("m" being the number of sites selected) is acquired, the process is terminated automatically. With this control, subtraction images S1–Sm of the predetermined sites are acquired automatically, and the hand switch 60 need not be continuously pressed throughout the process.

The defocusing voltage VD applied through the voltage switcher 40 may be made variable. Or, as shown in FIG. 4, plural types of defocusing voltages VD1–VDn may be used selectively. This may cope with a relatively wide range of sites including those having varied optimal defocusing voltages (e.g. a range from the head to the abdomen). Varied optimal defocusing voltages may be selected for different sites, with the horizontal movement of patient M. This feature provides the apparatus with high practical utility.

In above construction, the images picked up first of the respective sites (mask images D1–Dn) are all stored in the image memory 34. For example, the images picked up first of the respective sites may be stored successively in the image memory 34 by overwriting. That is, the image picked up first of each site is stored in the image memory 34 to retain this first image until the later image is picked up, in order to acquire a subtraction image for each site. Once a subtraction image is acquired for each site, the image picked up first for that site need not be retained in the image memory 34. Consequently, the image memory 34 may be used as a buffer memory for only temporarily storing the image picked up first of each site. The image picked up first of each successive site may be stored in the image memory 34 by overwriting. Then, the image memory 34 may have a reduced storage capacity just enough to store one image picked up.

As in the modification shown in FIG. 7 of the first embodiment, the subtraction images S1–Sn acquired for the respective sites may be stored successively in a predetermined storage location (SA) in the image memory 34. As in the modification shown in FIG. 8. mask images D1–Dn and live image F1–Fn picked up of the respective sites may be stored in the order of pickup in predetermined storage locations (FA and BA) in the image memory 34. Further, mask images D1–Dn and live images F1–Fn picked up of the respective sites, and subtraction images S1–Sn acquired for the respective sites, may be stored in the image memory 34 or the like.

As in the modification shown in FIG. 9. mask images D1–Dn and live images F1–Fn may be picked up of the respective sites and stored in the predetermined storage locations (FA and BA) in the image memory 34 while shifting the positional relationship between the patient M and the X-ray tube 11 and the like once. In a subsequent process, the mask images D1–Dn and live image F1–Fn stored may be subtracted to acquire subtraction images S1–Sn for the respective sites. With this construction also, the positional relationship between the patient M and the X-ray tube 11 and the like is shifted only once, and there is no need to inject the patient M with contrast material during the process, thus assuring a better throughput than the conventional apparatus. When computing subtraction image S1–Sn, the mask images D1–Dn and live images F1–Fn may simply be read successively from the respective storage locations FA and BA in the image memory 34. It is not necessary, as in the conventional apparatus, to search for a mask image and a live image matching each other with respect to a site. Thus, the subsequent process may be carried out in a reduced time.

In the subsequent process, a subtraction may be performed between an image integrating a plurality of mask images (the integrated image refers to a sum of mask images divided by the number of the images summed) and the live images. The integrated image is derived from mask images adjacent the mask image forming a pair with the live image to be subtracted. Assume, for example, that mask images D1–D10 and live images F1–F10 are picked up of 10 sites, and that subtraction image S4 is to be acquired for the fourth site. In this case, a subtraction is performed between an integrated image derived from mask images D2–D6 and the fourth live image F4. For acquiring the fifth subtraction image S5 for the fifth site, a subtraction is performed between an integrated image derived from mask images D3–D7 and the fifth live image F5. The subtraction images acquired in this way have an excellent signal-to-noise ratio.

The second embodiment may also be modified as shown in FIG. 10, to acquire a subtraction image for each site by emitting X rays from two or more directions.

Figure 14:
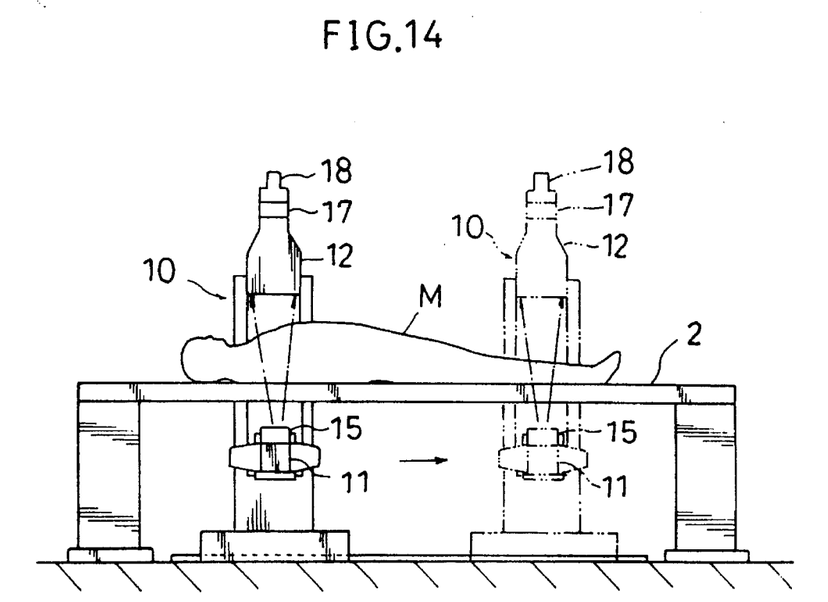
FIG. 14 is a view showing a modification relating to a relative shift between the patient and fluoroscopic device along the body axis of the patient.

In the constructions described hereinbefore, the patient M (top board 2) is horizontally movable relative to the fixed fluoroscopic device 10. However, as shown in FIG. 14, for example, the patient M (top board 2) may be fixed, with the fluoroscopic device 10 adapted movable relative to the patient M.

In the foregoing construction, the positional relationship between the patient M and the X-ray tube 11 and the like is shifted along the body axis of patient M. The second embodiment may be modified to shift this positional relationship about the body axis of patient M. In this case, the motor 19 in FIG. 2 is driven at a fixed rate to move the X-ray tube 11 and image intensifier 12 in the directions of arrow YJ, thereby to acquire subtraction images S1–Sn for predetermined sites. In this case, the motor 19 acts as the position shifting device. The positional relationship between the patient M and the X-ray tube 11 and the like may be shifted in other directions than the directions described herein, to acquire subtraction images S1–Sn for a plurality of sites.

The present invention may be embodied in other specific forms without departing from the spirit or essential attributes thereof and, accordingly, reference should be made to the appended claims, rather than to the foregoing specification, as indicating the scope of the invention.

What is claimed is:

1. A digital angiographic apparatus for picking up a mask image and a live image of a predetermined site, and deriving a subtraction image from a subtraction between the mask image and the live image, said apparatus comprising:

(a) fluoroscopic means including an X-ray tube and an image intensifier for irradiating a patient with X rays, and picking up fluoroscopic images of said patient;

(b) signal converting means for converting said fluoroscopic images into digital data;

(c) image storage means for storing said fluoroscopic images (images picked up) converted into digital data;

(d) voltage switching means switchable between a position for applying a focusing voltage to a focus adjusting electrode of said image intensifier to pick up an image in focus, and a position for applying a defocusing voltage to pick up an image out of focus to a degree of removing an image of a blood vessel from an image of the patient having contrast material injected;

(e) computing means for deriving a subtraction image from a subtraction between a mask image picked up when said defocusing voltage is applied to said focus adjusting electrode, and a live image picked up when said focusing voltage is applied to said focus adjusting electrode; and (f) control means for controlling said fluoroscopic means and other means to apply said defocusing voltage (or said focusing voltage) to said focus adjusting electrode, to pick up said mask image (or said live image) of said predetermined site of said patient with contrast material injected, to store at least said mask image (or said live image) in said image storage means, immediately thereafter to switch said voltage switching means to said position for applying said focusing voltage (or said defocusing voltage) to said focus adjusting electrode, to pick up said live image (or said mask image) of said predetermined site, and to apply said mask image and said live image to said computing means to acquire said subtraction image for said predetermined site.

2. A digital angiographic apparatus as defined in claim 1, wherein said fluoroscopic means includes plural sets of said X-ray tube and said image intensifier, said control means being operable to control said fluoroscopic means (said plural said of said X-ray tube and said image intensifier) and each of the other means to derive subtraction images of said predetermined site from multiple directions.

3. A digital angiographic apparatus as defined in claim 1, wherein said control means is operable to control said fluoroscopic means and each of the other means to pick up said mask image first of said predetermined site, to store at least said mask image in said image memory means, thereafter to pick up a plurality of live images of said predetermined site, and to cause said computing means to perform a subtraction between said mask image and each of said live images, thereby to acquire a plurality of subtraction images for said predetermined site.

4. A digital angiographic apparatus as defined in claim 3, wherein said control means is operable to store said subtraction images in said image storage means.

5. A digital angiographic apparatus as defined in claim 3, wherein said control means is operable to store said line images picked up later along with said mask image picked up first in said image storage means.

6. A digital angiographic apparatus as defined in claim 1, wherein said voltage switching means is switchable between a position for applying said focusing voltage to said focus adjusting electrode, and a position for applying plural types of defocusing voltages thereto, said control means being operable, when picking up said mask image, to select one of said defocusing voltages for application to said focus adjusting electrode according to imaging conditions such as said site and said patient to be imaged.

7. A digital angiographic apparatus as defined in claim 1, wherein said computing means is operable to acquire said subtraction image by subtracting said mask image multiplied by coefficient "k" satisfying $0 \leq k \leq 1$, from said live image.

8. A digital angiographic apparatus as defined in claim 1, wherein said control means is operable to store said image picked up later along with said image picked up first in said image storage means.

9. A digital angiographic apparatus as defined in claim 1, wherein said control means is operable to store said subtraction image in said image storage means.

10. A digital angiographic apparatus for picking up mask images and live images of a plurality of predetermined sites of a patient by shifting a positional relationship between an X-ray tube/image intensifier and the patient, and deriving a subtraction image for each of the sites from a subtraction between the mask image and the live image of each site, said apparatus comprising:

(a) fluoroscopic means including said X-ray tube and said image intensifier for irradiating said patient with X rays, and picking up fluoroscopic images of said patient;

(b) signal converting means for converting said fluoroscopic images into digital data;

(c) image storage means for storing said fluoroscopic images (images picked up) converted into digital data;

(d) voltage switching means switchable between a position for applying a focusing voltage to a focus adjusting electrode of said image intensifier to pick up an image in focus, and a position for applying a defocusing voltage to said focus adjusting electrode to pick up an image out of focus to a degree of removing an image of a blood vessel from an image of the patient having contrast material injected;

(e) computing means for deriving a subtraction image from a subtraction between each mask image picked up when said defocusing voltage is applied to said focus adjusting electrode, and each live image picked up when said focusing voltage is applied to said focus adjusting electrode;

(f) position shifting means for shifting said positional relationship between said patient and said X-ray tube/image intensifier; and (g) control means for controlling said fluoroscopic means and other means to shift said positional relationship between said patient with contrast material injected and said X-ray tube/image intensifier, and each time said positional relationship reaches one of said predetermined sites of said patient, to apply said defocusing voltage (or said focusing voltage) to said focus adjusting electrode, to pick up said mask image (or said live image), to store at least said mask image (or said live image) in said image storage means, immediately thereafter to switch said voltage switching means to said position for applying said focusing voltage (or said defocusing voltage) to said focus adjusting electrode, to pick up and live image (or said mask image) of said predetermined site, and to apply said mask image and said live image to said computing means to acquire said subtraction image for each of said predetermined sites.

11. A digital angiographic apparatus as defined in claim 10, wherein said position shifting means is operable to shift said positional relationship at least along a body axis of said patient.

12. A digital angiographic apparatus as defined in claim 10, wherein said position shifting means is operable to shift said positional relationship at least about a body axis of said patient.

13. A digital angiographic apparatus as defined in claim 10, wherein said position shifting means is operable to stop shifting of said positional relationship temporarily when said mask image and said live image are picked up of each predetermined site.

14. A digital angiographic apparatus as defined in claim 10, wherein said voltage switching means is switchable between a position for applying said focusing voltage to said focus adjusting electrode, and a position for applying plural types of defocusing voltages thereto, said control means being operable, when picking up said mask image of each predetermined site, to select one of said defocusing voltages for application to said focus adjusting electrode according to imaging conditions such as said predetermined site and said patient to be imaged.

15. A digital angiographic apparatus as defined in claim 10, wherein said computing means is operable to acquire said subtraction image by subtracting said mask image multiplied by coefficient "k" satisfying $0 \leq k \leq 1$, from said live image.

16. A digital angiographic apparatus as defined in claim 10, wherein said control means is operable to store said subtraction image of each predetermined site in said image storage means.

17. A digital angiographic apparatus as defined in claim 10, wherein said control means is operable to store said image picked up later of each predetermined site along with said image picked up first in said image storage means.

18. A digital angiographic apparatus as defined in claim 17, wherein said subtraction image of each predetermined site is acquired by subtracting an integrated image of a plurality of mask images of each predetermined site and a plurality of sites adjacent thereto, from said live image of each predetermined site.

19. A digital angiographic apparatus as defined in claim 10, wherein said fluoroscopic means includes plural sets of said X-ray tube and said image intensifier, said control means being operable to control said fluoroscopic means (said plural said of said X-ray tube and said image intensifier) and each of the other means to derive subtraction images of each predetermined site from multiple directions.

20. A digital angiographic apparatus as defined in claim 10, wherein said control means is operable to store said image in said image storage means by overwriting.

\* \* \* \* \*